United States Patent [19]
Cibulka

[11] 3,952,739
[45] Apr. 27, 1976

[54] FAIL SAFE SYSTEM FOR A PATIENT TRIGGERED RESPIRATOR

[75] Inventor: Anthony B. Cibulka, Poynette, Wis.

[73] Assignee: AIRCO, Inc., Montvale, N.J.

[22] Filed: Oct. 21, 1974

[21] Appl. No.: 516,567

[52] U.S. Cl............... 128/145.8; 128/DIG. 17; 340/279
[51] Int. Cl.² .................................. A61M 16/00
[58] Field of Search........... 128/145.5, 145.6, 145.8, 128/142.2, DIG. 17; 340/279, 421

[56] References Cited
UNITED STATES PATENTS

| | | | |
|---|---|---|---|
| 2,830,580 | 4/1958 | Saklad et al. | 128/DIG. 17 |
| 3,191,595 | 6/1965 | Wilson | 128/145.5 |
| 3,357,428 | 12/1967 | Carlson | 128/145.8 |
| 3,566,387 | 2/1971 | Schoener et al. | 128/145.5 |
| 3,595,228 | 7/1971 | Simon | 128/145.5 |
| 3,611,178 | 10/1971 | McConnell | 128/142.2 |
| 3,678,494 | 7/1972 | Setser | 340/279 |

Primary Examiner—Robert W. Michell
Assistant Examiner—Lee S. Cohen
Attorney, Agent, or Firm—Roger M. Rathbun; Edmund W. Bopp; H. Hume Mathews

[57] ABSTRACT

A fail safe system for preventing erroneous activation of a device, such as a respirator, is provided to inhibit continuous or free running operation of the device as well as precluding activation of the device within an initial, predetermined portion of a phase in a cycle of operation. A circuit is provided for inhibiting the production of an output activation signal in the event that an input signal is continuously present or present at least at the start of a phase. In addition, a further circuit is provided for establishing a predetermined delay period commencing with the start of a phase for precluding the production of an output activation signal during such a period. Thus, only upon sensing the occurrence of a particular external condition after the aforementioned delay period has expired, will an output activation signal be produced.

11 Claims, 4 Drawing Figures

3,952,739

FAIL SAFE SYSTEM FOR A PATIENT TRIGGERED RESPIRATOR

BACKGROUND OF THE INVENTION

The present invention relates to apparatus for preventing the erroneous activation of a device and more particularly, to fail safe systems for inhibiting activation of a respirator upon the production of undesired or erroneous patient initiated trigger signals.

In order to assist the breathing efforts of a patient, respirator devices have been commonly utilized. Generally, respirator devices are adapted to operate on a two-phase cycle simulating the inspirative and expirative periods of the respirative cycle of a patient. Respirators may, for example, operate only during an inspirative period to provide a supply of air, or oxgen enriched air, to a patient, thereby reducing the expenditure of energy by a patient necessary to inhale an adequate amount of air. The respirator may be rendered inoperative during the expirative phase of a patient respirative cycle or, the respirator may be adapted to respond to the inhalative efforts of a patient occurring during the latter portion of a normal expirative phase. Thus, rapid breathing by a patient may be accommodated by activating a respirator in response to an inhalative effort of a patient occurring somewhat earlier than the controller programmed time for activation of the respirator in an inspirative phase.

Although respirator devices have been beneficial in assisting the respirative efforts of a patient, it is necessary to assure that such devices do not assume an inspirative phase of operation at a point in time abnormally early in an expirative phase, nor assume a continuous or free running condition whereby air is erroneously supplied after an almost instantaneous expirative phase. Accordingly, it is necessary to provide a fail safe capability with such respirator devices to avoid the foregoing undesirable effects which can result from undesired operation of a respirator device. As previously mentioned, a respirator device may be adapted to be operated in response to the inhalative effort of a patient during the expirative phase of a respirative cycle. Commonly, a patient trigger device is utilized to activate a respirator and a description of an exemplary patient trigger device suitable for use with the present invention is found in U.S. Pat. No. 3,896,800, which is assigned to the assignee of the present invention. Generally, such patient trigger devices include a transducing element for generating an appropriate electrical signal in response to the inhalative effort of a patient. The aforementioned transducer may take the form of a vacuum chamber having a flexible diaphragm forming one surface portion thereof with the chamber placed in communication with a patient by a suitable flexible hose or conduit. An opaque member such as a shutter is preferably mounted on the diaphragm such that in the absence of a vacuum created by a patient inhalative attempt, light generated from a suitable light source is precluded by the shutter from impinging on a light detecting device such as a light dependent resistor. However, upon commencement of an inhalative attempt by a patient, the diaphragm is translated and the shutter member is withdrawn from the light path between the source and light detecting device such that an appropriate electrical trigger signal is thereby generated by the detecting device. The aforedescribed light source, shutter and detecting device or any trigger device that produces an electrical conductivity signal where inspiratory effort is sensed may be utilized with the patient trigger apparatus described in the above-identified co-pending application and may be utilized in connection with the present invention as will be described in greater detail hereinafter.

OBJECTS OF THE INVENTION

Accordingly, it is an object of the present invention to provide apparatus for precluding the undesired activation of a device.

It is another object of the present invention to provide a fail safe system for precluding operation of a respirator device during a predetermined portion of a respirative cycle.

It is yet another object of the present invention to provide a fail safe system for a respirator to prevent the respirator from assuming a free running or continuously operative condition in the event that a patient trigger signal is continuously present or is present at least at initiation of the expiratory phase of a respirative cycle.

It is still a further object of the present invention to provide a fail safe system for a respirator to inhibit continuous or free running operation thereof in the event that a continuous patient trigger signal is erroneously produced due to a malfunction of a device for detecting patient inhalative attempts.

Other objects of the present invention will become apparent from the detailed description of an exemplary embodiment thereof which follows and the novel features of the present invention will be particularly pointed out in conjunction with the claims appended hereto.

SUMMARY

In accordance with one embodiment of the present invention apparatus for avoiding undesired or erroneous activation of a device is provided. The exemplary fail safe system according to the present invention includes means for producing an output signal for activating a device such as respirator, means for sensing the inspirative effort of a patient, means for inhibiting the production of said output signal abnormally early in the expirative phase of a respirative cycle, thereby precluding operation of a respirator device at a time at which receipt by a patient of a supply of air would be dangerous and means for inhibiting the production of an output signal for activating a respirator as a result of the production of a trigger signal at the commencement of, or continuously throughout the expirative phase of a patient respirative cycle. Preferably, a bi-level voltage source is effective to alternately provide distinct voltage levels of equal duration corresponding to first and second phases of the respirative cycle of a patient.

BRIEF DESCRIPTION OF THE DRAWINGS

The invention will be more clearly understood by reference to the ensuing detailed description of an exemplary embodiment thereof in conjunction with the following drawing in which.

DESCRIPTION OF PREFERRED EMBODIMENT

Figure 1:
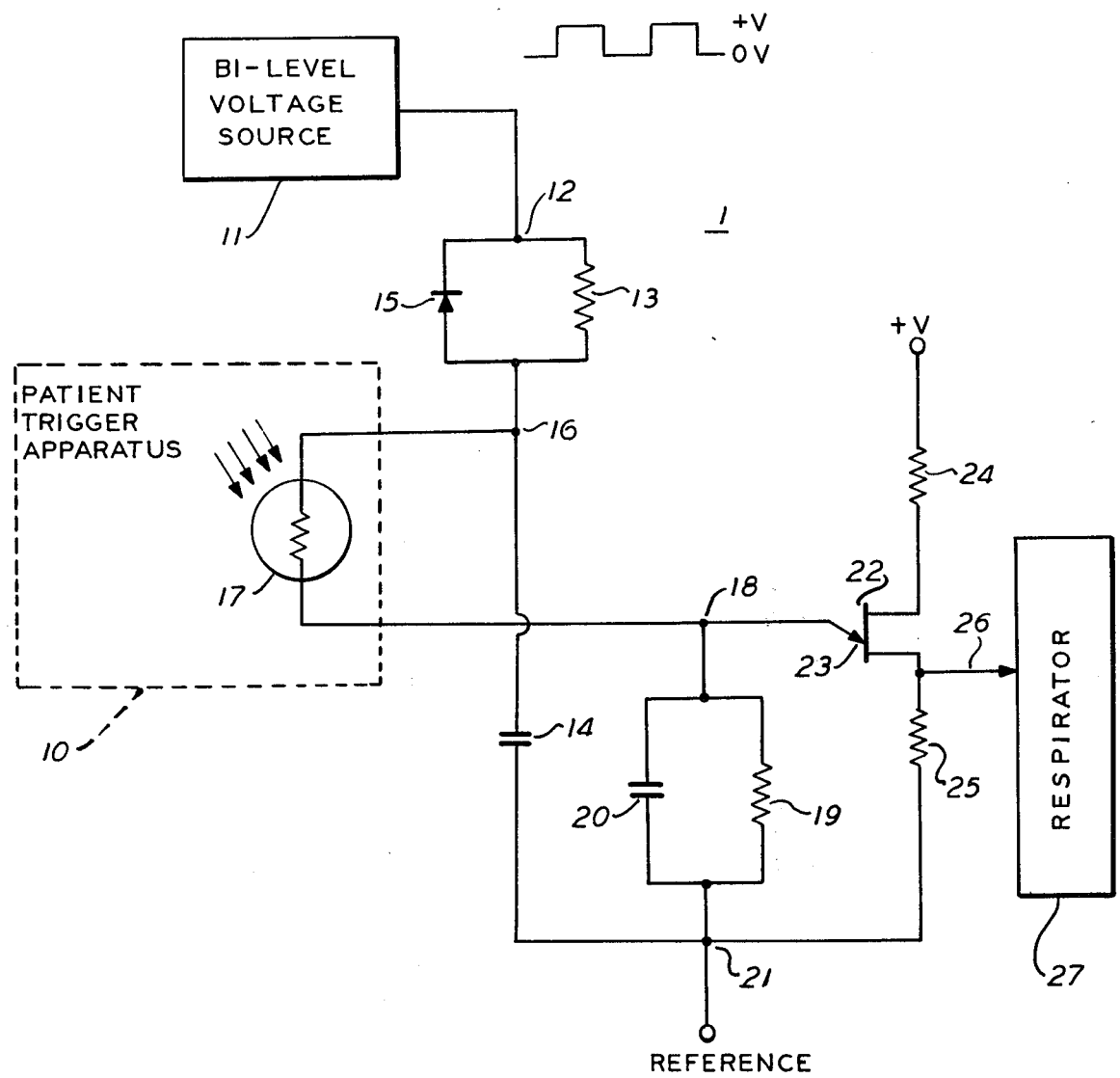
FIG. 1 is a schematic diagram of an exemplary electrical circuit for providing fail safe operation of a device such as a respirator.

Referring now to FIG. 1 of the drawing, there is illustrated an exemplary embodiment of a fail safe system 1 for assuring that a device is activated only under certain safe and desired circumstances. The exemplary fail safe system 1 essentially includes a bi-level voltage source 11; sensing means 17; an R-C charging circuit 13, 14; a voltage divider 13, 19; output signal means 22; and device 27. Bi-level voltage source 11 may take the form of any suitable power supply capable of generating alternate voltages of first and second levels, such as a square wave generator. Preferably, voltage source 11 will exhibit a constant duty cycle with one voltage level being a substantially constant positive potential and the other voltage level representing a reference or ground potential. In addition, it is preferred that the period of each phase corresponding to that of each of the foregoing voltage levels is established as coextensive with the normal inspirative and expirative phases of a patient respirative cycle. In order to effect a fail safe operation of a device such as respirator 27 in accordance with the teachings of the present invention, it is preferred to establish a first voltage level such as a voltage of +V during the expirative phase of a respirative cycle and produce a voltage of the second level, such as a reference or ground potential during the inspirative phase of such a cycle.

The output of voltage source 11 is applied to a junction 12 between a rectifier 15 which may comprise a conventional semiconductor diode and a resistor 13. The anode of recitifier 15 and the remaining terminal of resistor 13 are connected through junction 16 in series with a capacitor 14 thereby forming an R-C charging circuit between junction 12 and junction 21 which latter point is held at a reference or ground potential. A sensing means 17 is connected between junction 16 and a junction 18 and a parallel R-C circuit comprised of resistor 19 and capacitor 20 which in turn are additionally coupled to reference for ground potential 21. Sensing means 17 may take the form of a conventional electro-optical detecting element such as a light dependent resistor, a light responsive transistor, or electromechanical devices such as a microswitch or conventional contact points. Preferably, sensing means 17 is responsive to the occurrence of an external condition such as the inspirative efforts, i.e., an inhalative attempt, by a patient. As mentioned previously, sensing means 17 may form a portion of a patient trigger apparatus 10 described in U.S. Pat. No. 3,896,800 with radiation, such as visible light, being incident on means 17 during the actual inspirative effort of a patient. Preferably, the incidence of radiation such as visible light upon sensing means 17 will, for example, be effective to switch sensing means 17 from a first or high impedance state to a second or low impedance state as will be described in greater detail hereinafter.

Output signal means 22 may comprise a threshold device such as a conventional unijunction transistor or Schmitt trigger well known to those skilled in the art. Output signal means 22 is preferably provided with an input or emitter 23 with the bases thereof coupled through appropriate resistors 24 and 25 to a positive potential +V and a reference potential 21, respectively. It will be appreciated that output signal means 22 is operative in a conventional manner to supply an output signal on line 26 upon the voltage developed at junction 18 and supplied to emitter 23 exceeding a predetermined threshold value. Of course, in the event that the potential developed at junction 18 is less than the aforementioned predetermined value, no output signal will be supplied to line 26.

Respirator 27 may take the form of a conventional device capable of supplying air or oxygen enriched air to a patient during an inspirative phase of a patient respirative cycle while normally remaining inactive during an expirative phase. Accordingly, respirator 27 may comprise a known device commercially available from Airco, Inc., Ohio Medical Products Division, Model No. 560.

It is preferred that respirator 27 be capable of operation in a first mode whereby inspirative and expirative phases of a respirative cycle occur independent of any action or inaction on the part of a patient or in a second mode wherein the inspirative phase of operation may be initiated in the latter portion of a prior expirative phase as will be described in connection with the operation of the exemplary fail safe system illustrated in FIG. 1. It will be understood that operation of respirator 27 in the second mode will require that inhalative assistance be provided to a patient only after a predetermined initial portion of the expirative phase has elapsed in order to avoid any danger to the patient occurring from the abnormally early, and hence undesired, receipt of air as the patient is attempting to expirate. It will be understood that operation of respirator 27 in the inspiratory phase in either the first or second mode will be controlled independently of voltage source 11 and therefore, the output of voltage source 11 is held at a reference level during this phase of the respiratory cycle.

Figure 2:
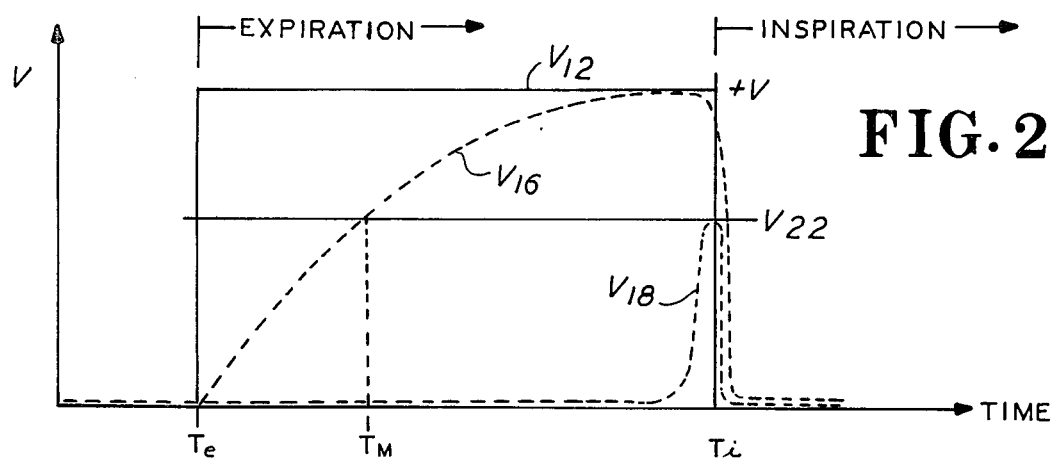
FIG. 2 is a graphical representation of voltages at certain circuit junctions of the exemplary circuit depicted in FIG. 1 during the normal operation thereof.
Figure 3:
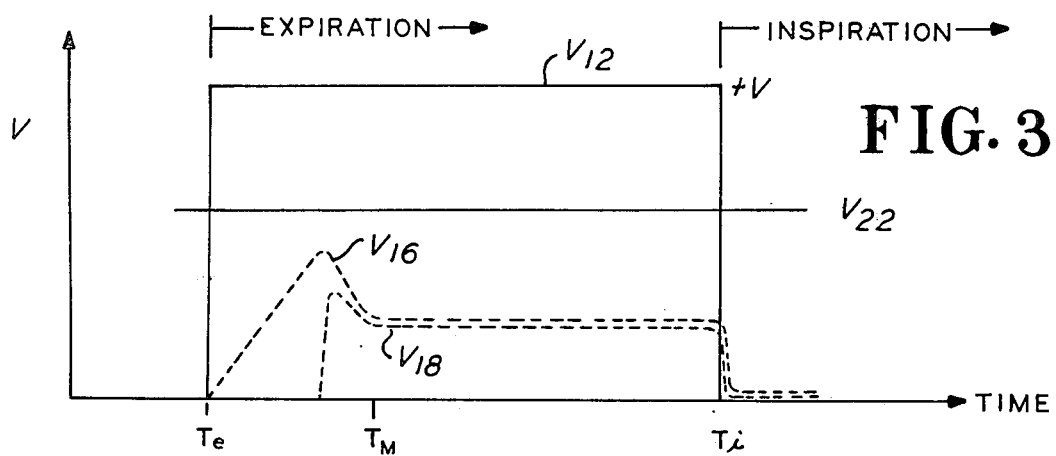
FIG. 3 is a graphical representation of the voltages depicted in FIG. 2 wherein an external condition such as the inspirative effort of a patient is sensed abnormally early during one phase, such as the expirative phase, of respirator operation.
Figure 4:
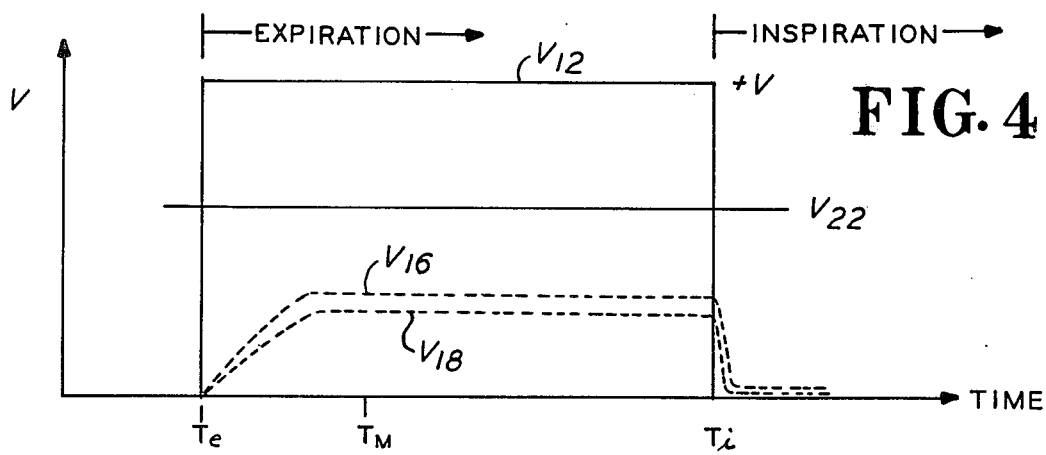
FIG. 4 is a graphical representation of the voltages depicted in FIGS. 2 and 3 wherein an external condition is sensed at the initiation of one phase, such as the expirative phase, of a respirative cycle.

The operation of the exemplary fail safe system illustrated in FIG. 1 will now be described with reference to FIGS. 2–4 wherein the voltages developed at junctions 16 and 18 are graphically represented under several conditions that may occur during an expirative phase, a positive potential +V is supplied to the charging circuit comprised of resistor 13 and capacitor 14. Accordingly, the voltage developed at junction 16 will increase toward +V with the level to which capacitor 14 charges being determined by resistor 13 and the combination of sensing means 17 and elements connected to junction 18. As sensing means 17 normally exhibits a high impedance, i.e., essentially non-conductive at the commencement of the expirative phase, capacitor 14 charges to a potential approximately equal to the voltage at junction 12 which voltage readily exceeds the threshold value of output signal means 22. Upon the voltage developed at junction 16 exceeding a voltage of $V_{22}$ (the predetermined threshold value of output signal means 22) respirator 27 is conditioned to be activated into an inspirative phase upon a patient attempt to inhale as detected by sensing means 17. Thus, in the event that a patient attempts to inhale during an expirative phase subsequent to time $T_m$, the moment at which the voltage at junction 16 exceeds the threshold value $V_{22}$, sensing means 17 will be switched from a first, high impedance state to a second low impedance state, thereby enabling the voltage developed on capacitor 14 to be also developed at resistor 19 and capacitor 20, which in turn will supply a voltage exceeding the predetermined threshold value of output signal means 22 and hence, produce an output signal on line 26 for activating respirator 27. In FIG. 2, an attempt of a patient to inhale is depicted as occurring at time $T_i$, and thus commencement of a normal inspirative phase of a respirative cycle will occur. It will be understood, however, that by selecting capacitor 14 to exhibit a capacitance substantially greater than the capacitance of capacitor 20, an adequate charge will be transferred to enable the voltage developed across resistor 19 and capacitor 20 to exceed the predetermined threshold value of output signal means 22. Accordingly, the fail safe circuit illustrated in FIG. 1 enables the production of an output or activating signal on line 26 upon detection of an inspirative attempt by a patient occurring after time $T_m$ in the expirative phase of a respiratory cycle. In addition, during the inspiratory phase, the output of voltage source is forced to a reference potential, e.g., 0 volts, such that the positive charge on capacitor 14 is discharged through rectifier 15 with capacitor 14 held at or near the reference voltage throughout the inspiratory phase. During this phase the supply of air to a patient is controlled by the controller logic of respirator 27, as previously mentioned.

Operation of the exemplary fail safe system illustrated in FIG. 1 upon a patient attempt to inhale at a moment in the expirative phase between the initiation thereof and a minimum time $T_m$ which, as noted above, is appropriately established as the time necessary for capacitor 14 to charge to a potential equal to the predetermined threshold value $V_{22}$. Referring now to FIG. 3, it will be appreciated that upon initiation of an expirative phase, the potential +V supplied by source 11 will cause capacitor 14 to charge thereby developing a corresponding voltage $V_{16}$ at junction 16. Upon detection of an inhalative attempt of a patient before time $T_m$ has elapsed, i.e., abnormally early in the expirative phase, sensing means 17 is switched from the aforesaid high impedance state to a low impedance state thereby transferring the portion of the charge stored on capacitor 14 such that approximately equal voltages are developed across capacitors 14 and 20. The voltage developed at junction 18 will rise rapidly as illustrated in FIG. 3, although as the voltage $V_{16}$ is less than the predetermined threshold value $V_{22}$, no output will be supplied to line 26 and thus, respirator 27 will not be activated. For the duration of the expirative phase, capacitors 14 and 20 will discharge through resistor 19 to a substantially constant level which will be established by the voltage divider action of resistors 13 and 19 as will be described in greater detail hereafter. Accordingly, it will be appreciated that upon a patient attempt to inhale during an expirative phase, or upon the detection of a condition which erroneously reflects such an attempt to inhale prior to a predetermined minimum time $T_m$ elapsing in the expirative phase, respirator 27 is inhibited from supplying air to a patient and hence, a fail safe effect is achieved.

The possible operating condition wherein either an actual or an apparent attempt by a patient to inhale abnormally early in an expirative phase, has been described in connection with FIG. 3. However, due to possible malfunctions of a pressure sensing transducer in the patient trigger apparatus, it is possible that sensing means 17 will continuously be improperly maintained in a low impedance condition, which in the absence of appropriate safeguards such as the fail safe system according to the present invention, would enable the charging of capacitors 14 and 20 almost instantaneously after the commencement of an expirative phase, thereby providing a potential at junction 18 exceeding the predetermined threshold value of output signal means 22 and hence supplying an output signal on line 26 effective to activate respirator 27. However, the foregoing problem of detecting an apparent inspirative attempt or at least an inspirative attempt virtually at the initiation of an expirative phase is solved by the fail safe system according to the present invention. Thus, in the event that sensing means 17 detects an actual or apparent inspirative attempt upon the initiation of an expirative phase, sensing means 17 is switched to a low impedance condition which thereby serves to couple junction 16 to junction 18 and limits the voltage which may develop across capacitors 14 and 20 by the voltage divider action of resistors 13 and 19. Thus, by selecting the value of resistor 13 to be substantially greater than the value of resistor 19, the positive potential +V is divided such that a fraction thereof substantially less than the predetermined threshold value $V_{22}$ is developed at junction 18. Accordingly, notwithstanding the detection of a continuous, and hence erroneous inspirative attempt by a patient, and particularly, detection of such an attempt at the initiation of an expirative phase, the potential developed at junction 18 and hence, the voltage supplied to emitter 23 of output signal means 22 is ineffective to cause an output signal to be generated on line 26 and hence, respirator 27 is maintained in an inactivated condition until the termination of the controller mode expiration phase at which point the respirator will automatically resume operation in the inspirative phase independently of any patient inhalative attempts. In addition, it will be appreciated that similar operation of respirator 27 will be effected at the end of an expirative phase notwithstanding an attempt by the patient to inhale abnormally early in such phase as was previously discussed in connection with FIG. 3.

It has been found that a suitable and effective fail safe system may be provided in accordance with the teachings of the present invention by utilizing passive circuit elements of the following values and active circuit elements of the following types:

| Resistor 13 | = 100 k ohms. | Sensing means 17 | = LDR 704 |
| " 19 | = 47 k ohms. | Rectifier 15 | = IN4148 |
| Capacitor 14 | = 4 mfd. | Unijunction Transistor 22 | = 2N4852 |
| " 20 | = 0.1 mfd. | +V | = 22 v. |

Although the present invention has been described in terms of a fail safe system for preventing erroneous and undesired operation of a respirator 27, it will be understood that this system may be utilized with other devices than a respirator, particularly wherein activation of such devices is to be precluded during certain predetermined time periods.

While the present invention has been particularly described in terms of specific embodiments thereof, it will be understood that numerous variations upon the invention are now enabled to those skilled in the art, which variations are yet within the scope of the instant teaching. Accordingly, the present invention is to be broadly construed and limited only by the scope and spirit of the claims now appended hereto.

I claim:

1. A fail safe system for preventing erroneous inspiratory operation of a respirator during the expiratory phase of a patient respiratory cycle comprising:
   means for supplying a potential during the expiratory phase of said respiratory cycle;
   sensing means coupled to said potential means for detecting an inspiratory effort of a patient during said expiratory phase;
   threshold means connected to said sensing means for producing an output signal for activating said respirator in response to said sensing means detecting said inspiratory effort;
   circuit means connected to said sensing means and to said threshold means for precluding the production of said output signal in response to said sensing means detecting said inspiratory effort before a predetermined portion of said expiratory phase has elapsed; and
   means coupled to said threshold means and said sensing means for inhibiting production of said output signal upon said sensing means detecting an inspiratory effort at the start of said expiratory phase.

2. A system as defined in claim 1 wherein said means for supplying a potential comprises voltage source means for producing high and low level signals of equal duration corresponding to said expiratory and inspiratory phases, respectively, of said respiratory cycle.

3. A system as defined in claim 2 wherein said sensing means comprises switching means for exhibiting a high impedance in the absence of said inspiratory effort and a low impedance upon the occurrence of said inspiratory effort.

4. A system as defined in claim 3 in which said circuit means comprise a series R-C network having a resistor and a capacitor connected between said voltage source means and a reference potential.

5. A system as defined in claim 4 in which said threshold means is provided with an input terminal and said sensing means is connected between said input terminal and the junction between said resistor and capacitor.

6. A system as defined in claim 5 wherein said inhibit means comprises a further resistor connected between said input terminal and said reference potential such that said resistor and said further resistor form a voltage divider network whereby the voltage developed across said further resistor is supplied to said input terminal.

7. A system as defined in claim 6 wherein said threshold means comprises trigger means for producing said output signal in response to an input signal supplied thereto having a magnitude which exceeds a predetermined threshold value, wherein a potential developed across said further resistor of said voltage divider upon said sensing means exhibiting said low impedance at the start of said expiratory phase is supplied to said input terminal and is of a magnitude less than said predetermined value thereby inhibiting the production of said output signal by said trigger means.

8. A system as defined in claim 7 additionally including a further capacitor connected in parallel with said further resistor whereby upon occurrence of said inspiratory effort during said expiratory phase, the charge developed on said capacitor is transferred to said further capacitor such that the voltage developed across said further capacitor is supplied to said input terminal, wherein the charge transferred to said further capacitor upon said sensing means exhibiting said low impedance within the predetermined portion of said expiratory phase develops a voltage across said further capacitor having a magnitude less than said predetermined value whereby production of said output signal by said trigger means is precluded.

9. A system as defined in claim 8 wherein said trigger means comprises a unijunction transistor and said input terminal thereof comprises an emitter electrode coupled to said sensing means and to said further resistor and said further capacitor.

10. A fail safe system for preventing erroneous activation of a respirator comprising means for supplying a voltage during a period corresponding to the expiratory phase of a respiratory cycle; a series resistor-capacitor charging circuit coupled to said voltage supply means; means for sensing an attempt by a patient to inhale coupled to the junction between said resistor and capacitor; threshold means coupled to said sensing means for producing an activating signal upon the potential supplied to an input of said threshold means exceeding a predetermined value; respirator means coupled to said threshold means and adapted to be operated in response to said activating signal; and transfer means for transferring the potential of said capacitor to said input of said threshold means upon detection of said inhalative attempt with the magnitude of said transferred potential failing to exceed said predetermined threshold value until said capacitor has been charging for a predetermined initial portion of said period during which portion operation of said respirator means is to be avoided.

11. A system as defined in claim 10 additionally comprising means for inhibiting said threshold means from producing said activating upon said sensing means detecting inhalative attempt at the commencement of said period corresponding to said expiratory phase.

* * * * *